US009320657B2

(12) United States Patent
Long et al.

(10) Patent No.: US 9,320,657 B2
(45) Date of Patent: Apr. 26, 2016

(54) ABSORBENT ARTICLE HAVING INTERCONNECTED WAIST AND LEG BANDS

(71) Applicant: Kimberly-Clark Worldwide, Inc., Neenah, WI (US)

(72) Inventors: Andrew Long, Appleton, WI (US); Julie Paveletzke, Neenah, WI (US)

(73) Assignee: KIMBERLY-CLARK WORLDWIDE, INC., Neenah, WI (US)

(*) Notice: Subject to any disclaimer, the term of this patent is extended or adjusted under 35 U.S.C. 154(b) by 110 days.

(21) Appl. No.: 14/231,185

(22) Filed: Mar. 31, 2014

(65) Prior Publication Data
US 2015/0272789 A1    Oct. 1, 2015

(51) Int. Cl.
*A61F 13/15* (2006.01)
*A61F 13/20* (2006.01)
*A61F 13/49* (2006.01)

(52) U.S. Cl.
CPC . *A61F 13/49011* (2013.01); *A61F 2013/49046* (2013.01); *A61F 2013/49092* (2013.01)

(58) Field of Classification Search
USPC ............. 604/385.25, 385.26, 385.28, 385.29, 604/385.3
See application file for complete search history.

(56) References Cited

U.S. PATENT DOCUMENTS

| | | | |
|---|---|---|---|
| 2,310,367 A | 2/1943 | Harwood | |
| 2,313,595 A | 3/1943 | Snyder | |
| 2,705,010 A * | 3/1955 | Sires | A61F 13/49003 604/397 |
| 2,754,824 A * | 7/1956 | Blaufus | A41B 13/04 604/373 |
| 2,793,642 A * | 5/1957 | Andruhovici | A41B 13/04 604/397 |
| 3,019,446 A | 2/1962 | Wyss et al. | |
| 3,338,992 A | 8/1967 | Kinney | |
| 3,341,394 A | 9/1967 | Kinney | |
| 3,499,442 A | 3/1970 | Steinmetz | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |

(Continued)

FOREIGN PATENT DOCUMENTS

EP    0217032    4/1987
FR    2653453    4/1991

(Continued)

OTHER PUBLICATIONS

International Search Report and Written Opinion of International Application No. PCT/IB2015/051668, Jun. 8, 2015, 13 pages.

*Primary Examiner* — Michele M Kidwell
(74) *Attorney, Agent, or Firm* — Armstrong Teasdale LLP

(57) ABSTRACT

An absorbent article includes a front waist region, a back waist region, and a crotch region extending between the front and back waist regions. The front waist region has a front waist edge and the back waist region has a back waist edge. The front and back waist edges define a waist opening when the absorbent article is in a wear configuration. An elastomeric waist band extends around at least a portion of the waist opening adjacent the front and back waist edges and defines a circumference of the waist opening. Each leg cuff member of a pair of leg cuff members defines a respective leg opening when the absorbent article is in the wear configuration and operatively connected to the waist band such that movement of the waist band results in movement of the leg cuff members.

18 Claims, 6 Drawing Sheets

(56) References Cited

U.S. PATENT DOCUMENTS

| | | |
|---|---|---|
| 3,855,046 A | 12/1974 | Hansen et al. |
| 4,100,324 A | 7/1978 | Anderson et al. |
| 4,340,563 A | 7/1982 | Appel et al. |
| 4,397,646 A * | 8/1983 | Daniels ............. A61F 13/49004 604/381 |
| 4,663,220 A | 5/1987 | Wisneski et al. |
| 4,745,636 A | 5/1988 | Lunt |
| 4,850,988 A | 7/1989 | Aledo et al. |
| 4,850,992 A | 7/1989 | Amaral et al. |
| 4,940,464 A | 7/1990 | Van Gompel et al. |
| 5,046,272 A | 9/1991 | Vogt et al. |
| 5,104,116 A | 4/1992 | Pohjola |
| 5,224,405 A | 7/1993 | Pohjola |
| 5,226,992 A | 7/1993 | Morman |
| 5,284,703 A | 2/1994 | Everhart et al. |
| 5,350,624 A | 9/1994 | Georger et al. |
| 5,370,634 A | 12/1994 | Ando et al. |
| 5,382,400 A | 1/1995 | Pike et al. |
| 5,385,775 A | 1/1995 | Wright |
| 5,486,166 A | 1/1996 | Bishop et al. |
| 5,490,846 A | 2/1996 | Ellis et al. |
| 5,575,006 A | 11/1996 | Wolfe |
| 5,704,071 A | 1/1998 | Barclay et al. |
| 5,820,973 A | 10/1998 | Dodge, II et al. |
| 5,853,405 A | 12/1998 | Surprise |
| 5,855,573 A | 1/1999 | Johansson |
| 6,046,469 A * | 4/2000 | Yamazaki ........... H01L 27/1085 257/295 |
| 6,057,024 A | 5/2000 | Mleziva et al. |
| 6,406,469 B1 | 6/2002 | Brain et al. |
| 6,552,245 B1 | 4/2003 | Roessler et al. |
| 6,790,203 B2 * | 9/2004 | Een ..................... A61F 13/4942 604/364 |
| 6,916,750 B2 | 7/2005 | Thomas et al. |
| 6,969,378 B1 | 11/2005 | Vukos et al. |
| 6,969,441 B2 | 11/2005 | Welch et al. |
| 7,527,616 B2 * | 5/2009 | Miyamoto ........ A61F 13/49413 604/385.27 |
| 7,575,573 B1 | 8/2009 | Roe et al. |
| 7,721,356 B2 | 5/2010 | Utaka |
| 7,803,244 B2 | 9/2010 | Siqueira et al. |
| 8,002,760 B2 | 8/2011 | Ehrnsperger et al. |
| 8,333,749 B2 | 12/2012 | Tsang et al. |
| 8,361,913 B2 | 1/2013 | Siqueira et al. |
| 8,398,605 B2 | 3/2013 | Roe et al. |
| 9,050,216 B2 * | 6/2015 | Molander ........... A61F 13/5622 |
| 9,078,789 B2 * | 7/2015 | Wang .................. A61F 13/4906 |
| 2003/0114826 A1 | 6/2003 | Roessler et al. |
| 2004/0006326 A1 * | 1/2004 | Nakajima ........... A61F 13/5622 604/385.24 |
| 2004/0193134 A1 * | 9/2004 | Mueller ................ A61F 13/495 604/385.101 |
| 2009/0187156 A1 | 7/2009 | Anzalone |
| 2012/0042493 A1 | 2/2012 | Schmitz |
| 2012/0277713 A1 * | 11/2012 | Raycheck ........... A61F 13/4942 604/385.26 |
| 2014/0005621 A1 | 1/2014 | Roe et al. |

FOREIGN PATENT DOCUMENTS

| | | |
|---|---|---|
| GB | 962051 | 6/1964 |
| JP | 2001029389 | 2/2001 |
| WO | 0188245 | 11/2001 |
| WO | 2005037160 A1 | 4/2005 |

* cited by examiner

ABSORBENT ARTICLE HAVING INTERCONNECTED WAIST AND LEG BANDS

FIELD

The present disclosure relates generally to absorbent articles intended for personal wear, and more particularly to absorbent articles having interconnected waist and leg bands.

BACKGROUND

Exemplary pull-on absorbent articles include training pants, diaper pants, incontinence products, disposable underwear, medical garments, absorbent swim wear, and the like. Pull-on type absorbent articles are absorbent articles configured to be donned like conventional underwear. That is, by pulling the article up around the wearer's legs. Some known pull-on type absorbent articles can be doffed by sliding the pant down around the wearer's legs. Other known pull-on type absorbent articles can be removed from the wearer by tearing the article along their sides. Still other known pull-on type absorbent articles can be removed using refastenable fasteners (e.g., hook and loop fasteners) disclosed on the sides of the article.

Absorbent articles typically include an outer cover, an inner liner, and an absorbent assembly disposed between the outer cover and the inner liner. In order to inhibit leakage of exudates released by the article's wearer, it is known to include elastic waist bands and leg cuffs on the articles adjacent a waist opening and leg openings, respectively, of the article. Conventional waist bands typically include an elastomeric material extending entirely or partially around the waist opening of the article, and conventional leg cuffs typically include an elastomeric material extending entirely or partially around the leg openings of the article.

During use of the articles, the elastomeric material forming the leg cuffs provides a seal against the wearer's body (i.e., the upper thighs of the wearer) to inhibit the transverse flow of exudates. However during use and particularly after prolonged use of the article, the elastomeric material forming the leg cuffs may lose its ability to fully or otherwise sufficiently retract thereby compromising the seal formed against the wearer's body. The lack of an adequate seal may result in the undesirable leakage of exudates from the absorbent article. As one can readily appreciate, leakage of exudates past the leg cuffs can result in the unwanted soiling the clothing, bedding, and person.

Moreover, if the elasticization of the leg cuffs is too great, the leg cuffs can irritate and/or mark the wearer's skin. That is, the wearer's skin can be adversely impacted when the tension and/or elongation of the leg cuffs results in too high of a pressure against the wearer's body when the seal is formed.

As a result, a need remains for leg cuffs that maintain a sufficient seal against the wearer's body during use and particularly prolonged use of the article. Moreover, there is a need for configured to provide an adequate seal against the wearer's body without irritating and/or marking the wearer's body.

SUMMARY

In one aspect, an absorbent article has a body-facing side and a garment-facing side. The absorbent article generally comprises a bodyside liner, an outer cover, an absorbent structure disposed between the outer cover and the bodyside liner, a front waist region, a back waist region, and a crotch region extending between the front waist region and the back waist region. The front waist region has a front waist edge and the back waist region has a back waist edge. The front and back waist edges define a waist opening of the absorbent article when the absorbent article is in a wear configuration. An elastomeric waist band extends around at least a portion of the waist opening adjacent the front and back waist edges and defines a circumference of the waist opening. Each leg cuff member of a pair of leg cuff members defines a respective leg opening when the absorbent article is in the wear configuration and operatively connected to the waist band such that movement of the waist band results in movement of the leg cuff members. Each of the leg cuff members has a lower, generally teardrop-shaped portion and an upper, generally "V" shaped portion extending between the teardrop-shaped portion and the waist band. The "V" shaped portion defines a first segment and a second segment spaced from the first segment by a distance D1. A ratio between the distance D1 and the circumference of the waist band is between 1:1.75 and 1:7 in a relaxed state of the wear configuration.

In another aspect, an absorbent article has a body-facing side and a garment-facing side. The absorbent article generally comprises a bodyside liner, an outer cover, and an absorbent structure disposed between the outer cover and the bodyside liner, a front waist region, a back waist region, and a crotch region extending between the front waist region and the back waist region. The front waist region has a front waist edge and the back waist region has a back waist edge. The front and back waist edges define a waist opening of the absorbent article when the absorbent article is in a wear configuration. An elastomeric waist band extends around at least a portion of the waist opening adjacent the front and back waist edges. The elastomeric waist band comprises a front waist elastic member disposed in the front waist region adjacent the front waist edge and a back waist elastic member bonded to the front waist elastic member disposed in the back waist region adjacent the back waist edge. Each leg cuff member of a pair of leg cuff members defines a respective leg opening when the absorbent article is in the wear configuration and operatively connected to the waist band such that movement of the waist band results in movement of the leg cuff members.

In yet another aspect, an absorbent article has a body-facing side and a garment-facing side. The absorbent article generally comprises a bodyside liner, an outer cover, and an absorbent structure disposed between the outer cover and the bodyside liner, a front waist region, a back waist region, and a crotch region extending between the front waist region and the back waist region. The front waist region has a front waist edge and the back waist edge has a second waist end. The front and back waist edges define a waist opening of the absorbent article when the absorbent article is in a wear configuration. An elastomeric waist band extends around at least a portion of the waist opening adjacent the first and second waist ends. Each leg cuff member of a pair of leg cuff members defines a respective leg opening when the absorbent article is in the wear configuration and operatively connected to the waist band such that movement of the waist band results in movement of the leg cuff members. Each of the leg cuff members extends along a respective side edge of the absorbent article from the front waist edge to the back waist edge when the absorbent article is in an unfolded and laid flat configuration.

BRIEF DESCRIPTION OF THE DRAWINGS

Corresponding reference characters indicate corresponding parts throughout the several views of the drawings.

DETAILED DESCRIPTION OF THE DRAWINGS

Figure 1:
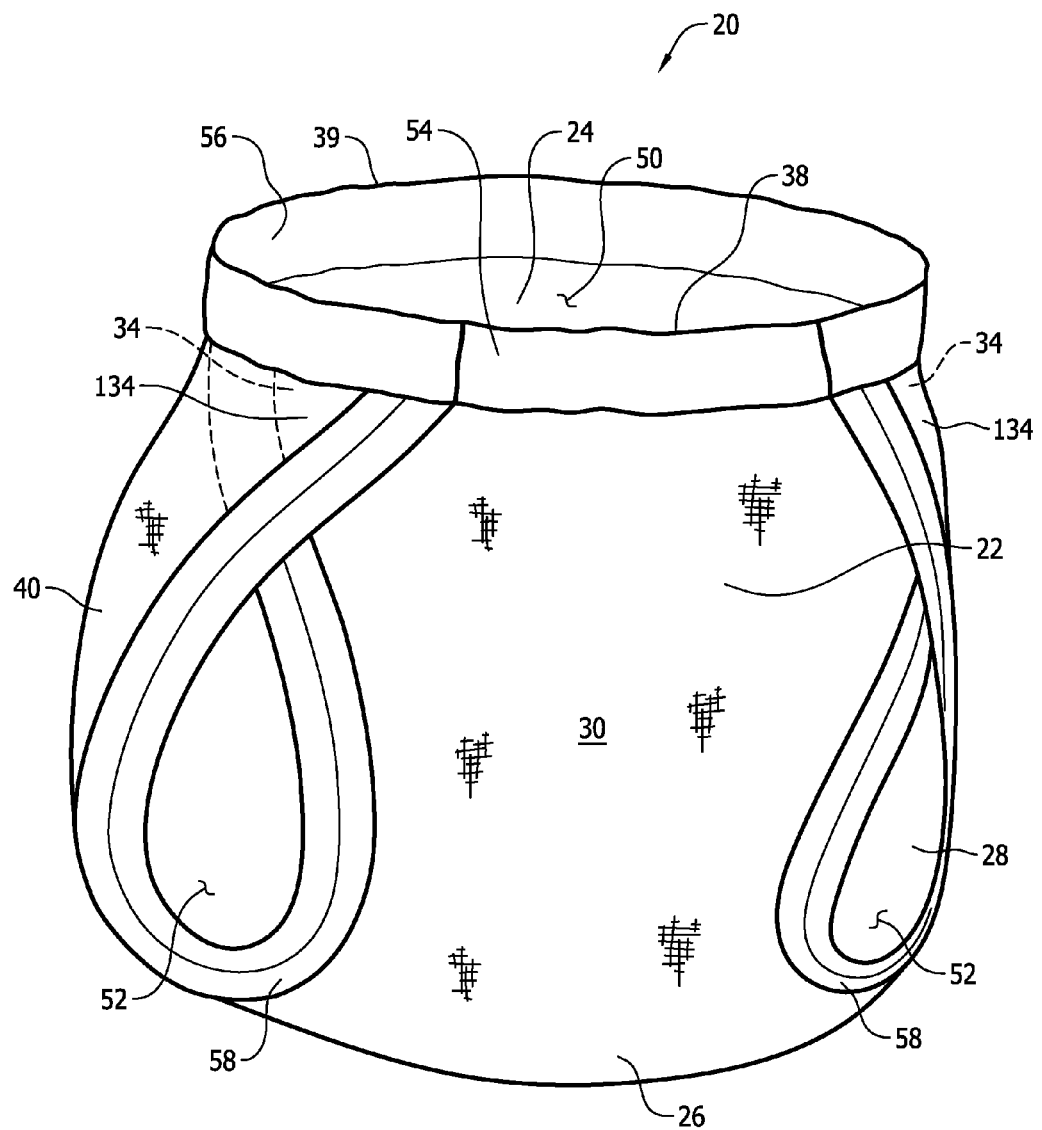
FIG. 1 is a perspective of one suitable embodiment of an absorbent article in the form of a diaper pant, the diaper pant having a waist band and a pair of leg cuff members wherein the leg cuff members are interconnected to the waist band.

Referring now to the drawings and in particular to FIG. 1, one suitable embodiment of an absorbent article is illustrated in the form of a child's diaper pant and is indicated generally in its entirety by the reference numeral 20. The term absorbent article generally refers to articles that may be placed against or in proximity to a body of a wearer to absorb and/or retain various exudates from the body. The absorbent diaper pant 20 may or may not be disposable. Disposable refers to articles that are intended to be discarded after a limited period of use instead of being laundered or otherwise conditioned for reuse. It is understood that the embodiments of the present disclosure are suitable for use with various other absorbent articles intended for personal wear, including but not limited to training pants, swim diapers, feminine hygiene products (e.g., sanitary napkins), incontinence products, medical garments, surgical pads and bandages, other personal care or health care garments, and the like without departing from the scope of the present disclosure.

Figure 2:
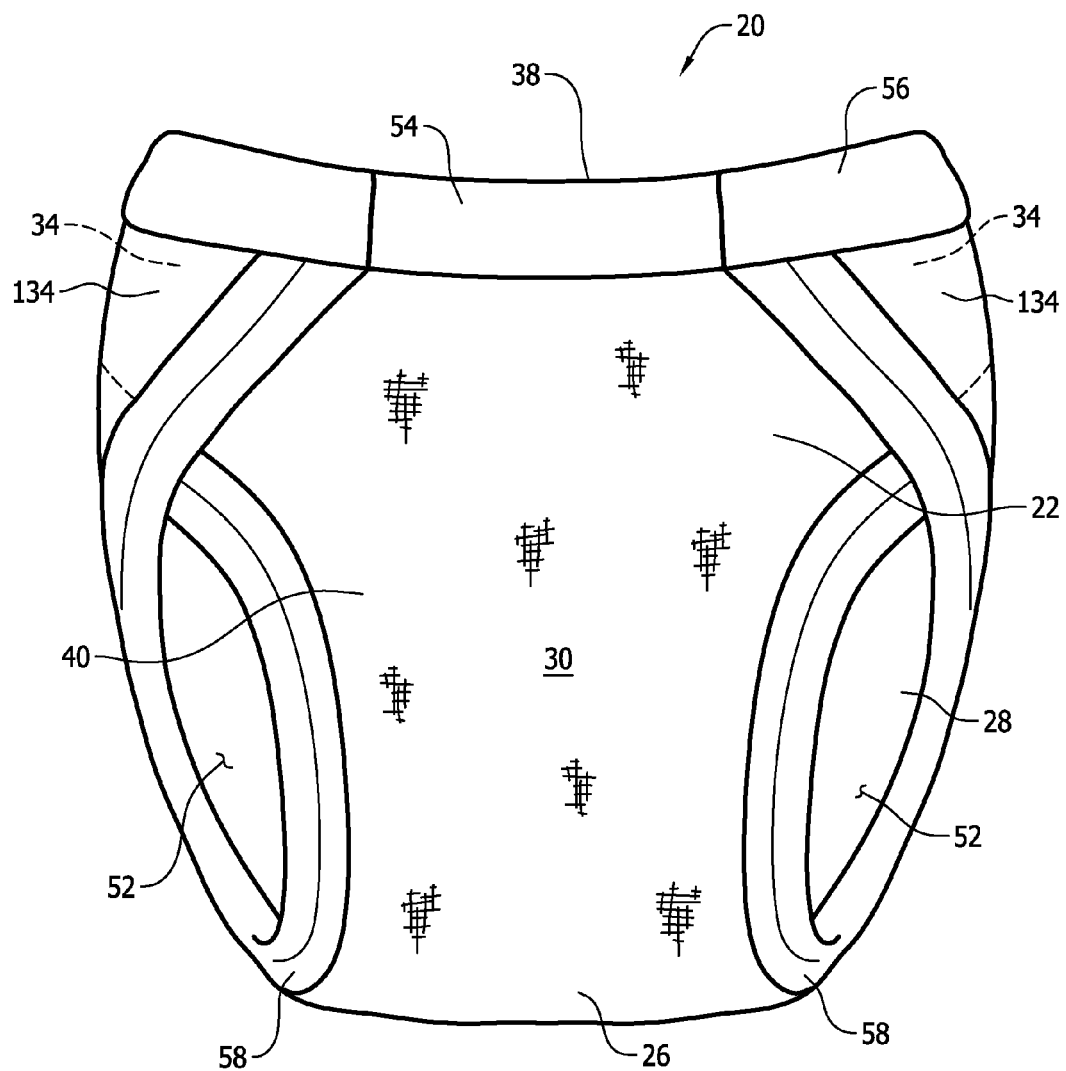
FIG. 2 is a front view of the diaper pant of FIG. 1.
Figure 3:
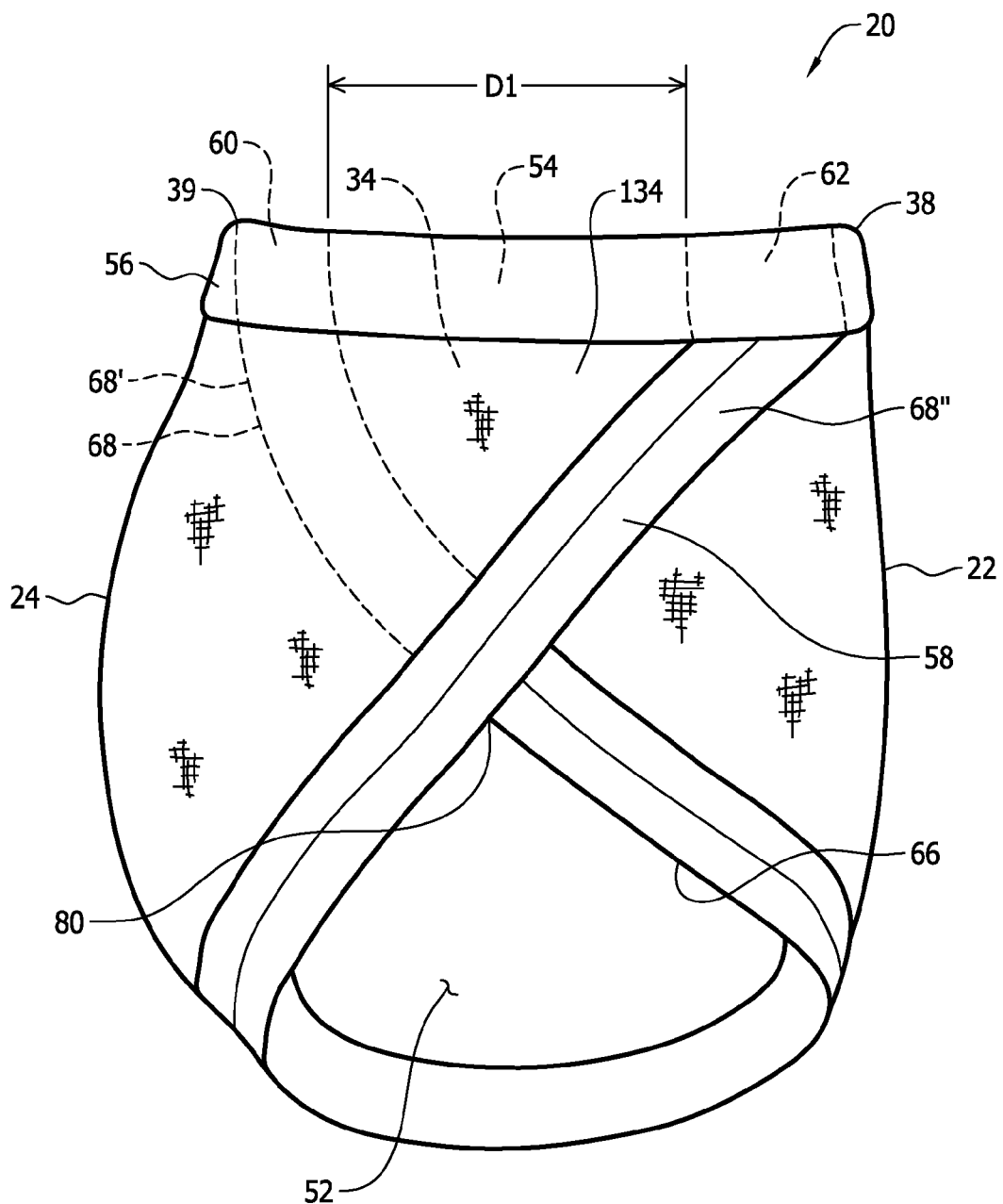
FIG. 3 is a side view of the diaper pant of FIG. 1.

The diaper pant 20 is illustrated in FIGS. 1-3 in a fully assembled configuration (broadly referred to herein as a "wear configuration" of the pant). The diaper pant 20 comprises a front waist region 22, a back waist region 24, a crotch region 26 extending longitudinally between and interconnecting the front and back waist regions along a longitudinal direction of the pant 20. With additional reference to FIGS. 4 and 5, an inner or body-facing surface 28 of the diaper pant 20 is configured for contiguous relationship with the wearer, and an outer or garment-facing surface 30 is opposite the inner surface. The diaper pant 20 also has a pair of laterally opposite side edges 36 and a pair of longitudinally opposite waist edges, respectively designated the front waist edge 38 and the back waist edge 39. The front waist region 22 is contiguous with the front waist edge 38, and the back waist region 24 is contiguous with the back waist edge 39.

Figure 4:
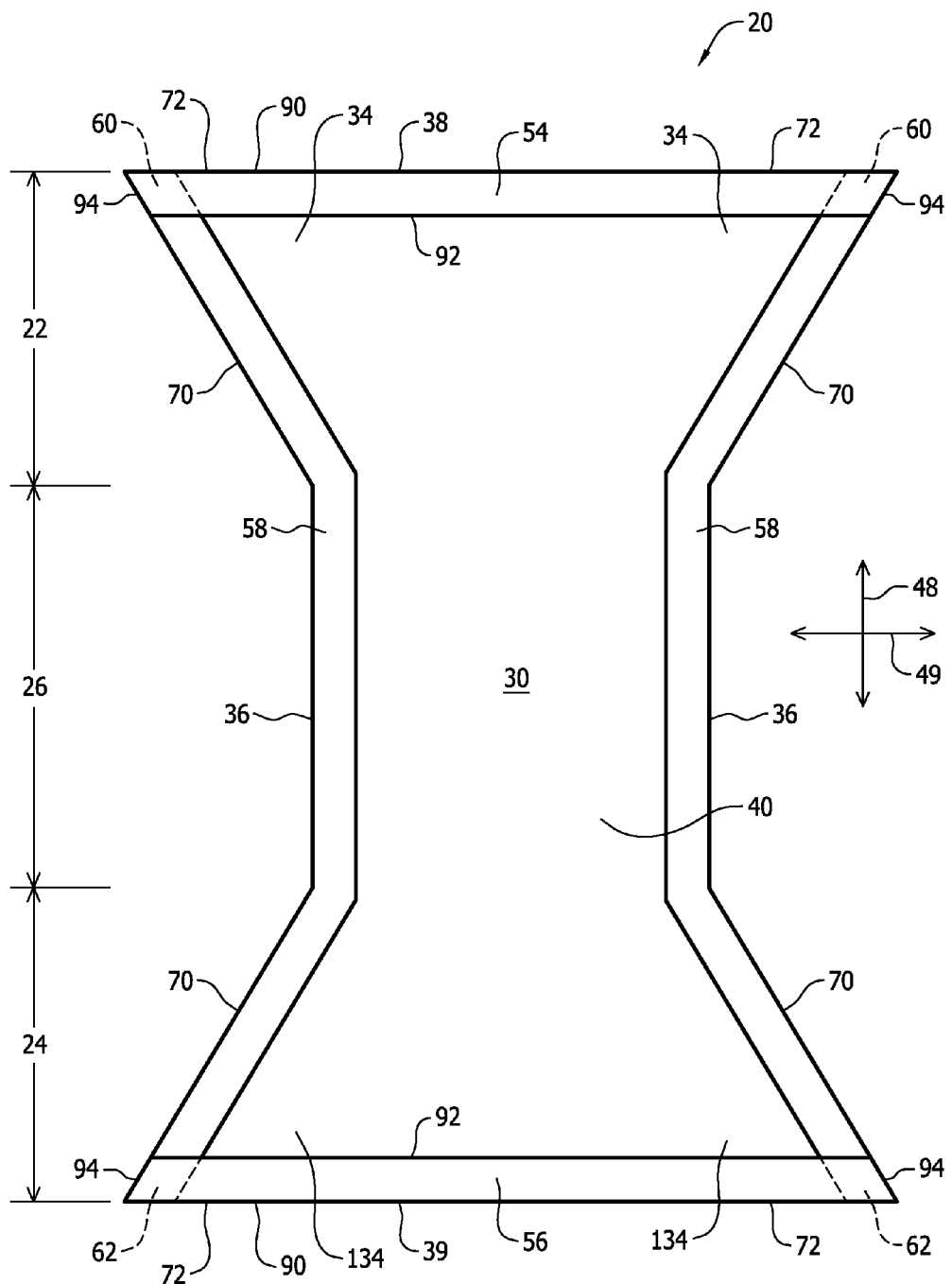
FIG. 4 is a bottom plan view of the diaper pant of FIG. 1 with the diaper pant in an unbonded, unfolded and laid flat condition, and showing a surface of the diaper pant adapted to face away from the wearer during use.
Figure 5:
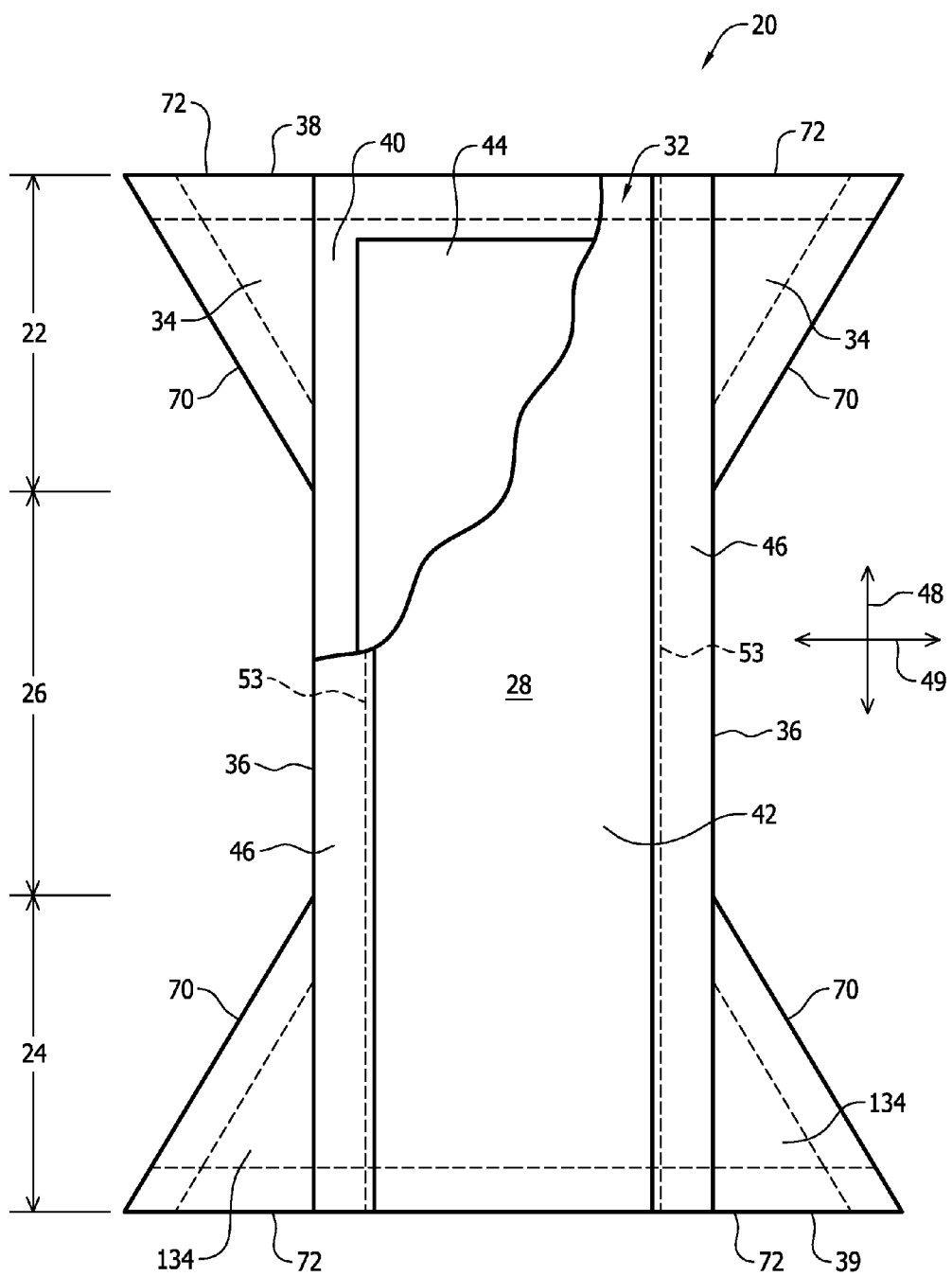
FIG. 5 is a top plan view similar to FIG. 2 but showing a surface of the diaper pant adapted to face the wearer during use, portions of the diaper pant being cut away to show underlying features.

With reference to FIGS. 4 and 5, the diaper pant 20 includes a central absorbent assembly, generally indicated at 32, which when laid flat as seen in FIGS. 4 and 5 can be rectangular. It is understood, however, that the absorbent assembly 32 can have any suitable shape. A pair of laterally opposite front ears 34 extends outward from the absorbent assembly 32 at the front waist region 22 (thereby forming transversely outer portions of the front waist region, and more broadly in part forming transversely opposite sides of the diaper pant 20). Laterally opposite back ears 134 extend outward from the absorbent assembly 32 at the back waist region 24 (thereby forming transversely outer portions of the back waist region, and together with the front ears 34 further defining the sides of the pant 20). Arrows 48 and 49 in FIGS. 4 and 5 depict the orientation of a longitudinal axis and a transverse or lateral axis, respectively, of the diaper pant 20.

The central absorbent assembly 32 of the illustrated embodiment comprises an outer cover 40 and a bodyside liner 42 connected to the outer cover 40 in a superposed relation by suitable means such as adhesives, ultrasonic bonds, thermal bonds, pressure bonds, or combinations thereof. An absorbent structure 44 (FIG. 5) is disposed between the outer cover 40 and the bodyside liner 42. A pair of containment flaps 46 (FIG. 5) is secured to the bodyside liner 42 for inhibiting the lateral flow of body exudates. Alternatively, the containment flaps 46 may be integrally formed with the bodyside liner 42. The central absorbent assembly 32 has opposite ends which form portions of the front and back waist edges 38 and 39, and opposite side edges which form portions of the side edges 36 of the diaper pant 20 (FIGS. 2 and 3).

In one suitable embodiment and as seen in FIGS. 1-5, the absorbent assembly 32 and the ears 34, 134 are integrally formed with one another. The integrally formed ears 34, 134 and absorbent assembly 32 include at least some common materials, such as the bodyside liner, outer cover, or combinations thereof. In the illustrated embodiment, for example, the ears 34 and 134 are formed integrally (i.e., as a single piece) with the outer cover. It is understood, however, that the ears 34 and 134 could be formed as separate discrete pieces and attached to the absorbent assembly 32.

In the illustrated embodiment and as seen in FIGS. 1-3, the front and back ears 34, 134 are non-releasably attached to one another in overlapping relationship using a suitable attachment method such as, for example, adhesive bonding, ultrasonic bonding, thermal bonding, pressure bonding, or combinations thereof. Specifically, in the illustrated embodiment, one of the front ears 34 is bonded to a respective one of the back ears 134 at a location generally adjacent the front and back waist edges 38, 39. The portions of the front and back ears 34, 134 spaced from the front and back waist edges 38, 39 (i.e., not adjacent the waist edges) are not bonded together. Thus, the majority of the front and back ears 34, 134 can move relative to each other during use of the pant 20. It is contemplated, however, that the front and back waist ears 34, 134 can be bonded together to any suitable extent.

In the illustrated embodiment, the back ears 134 overlap the front ears 34. It is understood, however, that the front ears 34 could overlap the back ears 134. It is also understood that in some suitable embodiments the front and back ears 34, 134 could be releasably attachable and/or detachable to each other. For example, the front and back ears 34, 134 could be releasably attachable and detachable from each other using any suitable refastenable fastening system (e.g., a hook and loop fastener system).

With the diaper pant 20 in the wear configuration, as illustrated in FIGS. 1-3, the diaper pant 20 defines a waist opening 50 and a pair of leg openings 52. The waist edges 38, 39 of the diaper pant 20 are configured to encircle the waist of the wearer and together define the waist opening 50 (FIG. 1). Portions of the side edges 36 in the crotch region 26 generally define the leg openings 52. The front waist region 22 comprises the portion of the diaper pant 20 which, when worn, is positioned at least in part on the front of the wearer while the back waist region 24 comprises the portion of the diaper pant 20 which is positioned at least in part on the back of the wearer. The crotch region 26 of the diaper pant 20 comprises the portion of the diaper pant 20 which is positioned between the legs of the wearer and covers the lower torso of the wearer. The ears 34, 134 comprise the portions of the diaper pant 20

(and more particularly of the front and back waist regions 22, 24) which, when worn, are positioned on the hips of the wearer.

The central absorbent assembly 32, which can be seen in FIG. 5, is configured to contain and/or absorb exudates discharged from the wearer. The outer cover 40 suitably comprises a material that is substantially liquid impermeable. The outer cover 40 can be a single layer of liquid impermeable material, but more suitably comprises a multi-layered laminate structure in which at least one of the layers is liquid impermeable. For instance, the outer cover 40 can include a liquid permeable outer layer and a liquid impermeable inner layer that are suitably joined together by an adhesive, ultrasonic bonding, thermal bonding, pressure bonding, or combinations thereof. Suitable adhesives can be applied continuously or intermittently as beads, a spray, parallel swirls, or the like. The liquid permeable outer layer can be any suitable material, including materials that provide a generally cloth-like texture. The outer layer may also be made of those materials of which the liquid permeable bodyside liner 42 is made. While it is not a necessity for the outer layer to be liquid permeable, it is suitable that it provides a relatively cloth-like texture to the wearer.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver.

If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. One suitable "breathable" material is composed of a microporous polymer film or a nonwoven fabric that has been coated or otherwise treated to impart a desired level of liquid impermeability.

It is also contemplated that the outer cover 40 may be stretchable, and more suitably elastic. In particular, the outer cover 40 is suitably stretchable and more suitably elastic in at least the transverse, or circumferential direction of the pant 20. In other embodiments the outer cover 40 may be stretchable, and more suitably elastic, in both the transverse and the longitudinal direction.

The liquid permeable bodyside liner 42 is illustrated as overlying the outer cover 40 and absorbent structure 44, and may, but need not, have the same dimensions as the outer cover 40. The bodyside liner 42 is suitably compliant, soft feeling, and non-irritating to the wearer's skin. The bodyside liner 42 is also sufficiently liquid permeable to permit liquid body exudates to readily penetrate through its thickness to the absorbent structure 44. Further, the bodyside liner 42 can be less hydrophilic than the absorbent structure 44 to present a relatively dry surface to the wearer and permit liquid to readily penetrate through its thickness. The hydrophilic/hydrophobic properties can be varied across the length, width and/or depth of the bodyside liner 42 and absorbent structure 44 to achieve the desired wetness sensation or leakage performance.

The bodyside liner 42 can be manufactured from a wide selection of web materials, such as porous foams, reticulated foams, apertured plastic films, woven and non-woven webs, or a combination of any such materials. For example, the bodyside liner 42 may comprise a meltblown web, a spunbonded web, or a bonded-carded-web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal center line.

The bodyside liner 42 may also be stretchable, and, more suitably, it may be elastomeric. In particular, the bodyside liner 42 is suitably stretchable and more suitably elastomeric in at least the transverse 49, or circumferential direction of the pant 20. In other embodiments the bodyside liner 42 may be stretchable, and more suitably elastomeric, in both the transverse 49 and the longitudinal 48 directions.

Suitable elastomeric materials for construction of the bodyside liner 42 can include elastic strands, LYCRA elastics, cast or blown elastic films, nonwoven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon of Cleveland, Ohio), or PEBAX elastomers. The bodyside liner 42 can also be made from extensible materials as are described in U.S. patent application Ser. No. 09/563,417 filed on May 3, 2000 by Roessler et al. (now U.S. Pat. No. 6,552,245) or from biaxially stretchable materials as are described in U.S. patent application Ser. No. 09/698,517 filed on Oct. 27, 2000 by Vukos et al. (now U.S. Pat. No. 6,969,378), both of which are hereby incorporated by reference.

The absorbent structure 44 is suitably compressible, conformable, non-irritating to a wearer's skin, and capable of absorbing and retaining liquids and certain body wastes. For example, the absorbent structure 44 may comprise cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent structure comprises a matrix of cellulosic fluff and superabsorbent hydrogel-forming particles. The cellulosic fluff may include a blend of wood pulp fluff. Suitable types of fluff include, for example, fluff pulp commercially available from Weyerhaeuser Company of Federal Way, Wash., U.S.A. under the designation FR416 (7.5 percent Moisture) and CF416 (7.5 percent Moisture).

The materials may be formed into a web structure by employing various conventional methods and techniques. For example, the absorbent structure 44 may be formed by a dry-forming technique, an air forming technique, a wet-forming technique, a foam-forming technique, or the like, as well as combinations thereof. Furthermore, the absorbent structure 44 may itself encompass multiple layers in a Z-direction (e.g., thickness) of the absorbent structure 44. Such multiple layers may take advantage of differences in absorbent capacity, such as by placing a lower absorbent capacity material layer closer to the bodyside liner 42 and a higher absorbent capacity material closer to the outer cover 40. Likewise, discrete portions of a single-layered absorbent structure may encompass higher capacity absorbents, and other discrete portions of the structure may encompass lower capacity absorbents.

Superabsorbent material is suitably present in the absorbent structure 44 in an amount of from about 0 to about 100 weight percent based on total weight of the absorbent structure 44. The absorbent structure 44 may suitably have a density within the range of about 0.10 to about 0.60 grams per cubic centimeter. Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and preferably is capable of absorbing more than about 25 times its weight in liquid. Suitable superabsorbent materials are readily available from various suppliers. For example, Hysorb T 9700 superabsorbent, which is commercially available from BASF of Ludwigshafen, Germany, or Favor SXM 5600 superabsorbent, which is commercially available from Evonik of Essen, Germany.

The absorbent structure 44 may alternatively comprise a coform material. The term "coform material" generally refers to composite materials comprising a mixture or stabilized matrix of thermoplastic fibers and a second non-thermoplastic material. As an example, coform materials are made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the meltspun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference.

In one suitable embodiment, the absorbent structure 44 is stretchable so as not to inhibit the stretchability of other components to which the absorbent structure may be adhered, such as the outer cover 40 and the bodyside liner 42. After being formed or cut to a desired shape, the absorbent structure 44 may be wrapped or encompassed by a suitable wrap (not shown) that aids in maintaining the integrity and shape of the absorbent structure 44. As best seen in FIG. 4, the absorbent structure 44 of the illustrated embodiment is generally rectangular, although the absorbent structure 44 can have any suitable shape and size.

The central absorbent assembly 32 may also include a surge management layer (not shown) located adjacent the absorbent structure 44 (e.g., between the absorbent structure 44 and the bodyside liner 42) to help decelerate and diffuse surges or gushes of liquid that may be rapidly introduced into the absorbent structure 44 of the diaper pant 20 by the wearer. Desirably, the surge management layer can rapidly accept and temporarily hold the liquid prior to releasing the liquid into the storage or retention portions of the absorbent structure 44. Examples of suitable surge management layers are described in U.S. Pat. No. 5,486,166 issued Jan. 23, 1996 to Bishop et al.; U.S. Pat. No. 5,490,846 issued Feb. 13, 1996 to Ellis et al.; and U.S. Pat. No. 5,820,973 issued Oct. 13, 1998 to Dodge, II et al., the entire disclosures of which are hereby incorporated by reference.

The central absorbent assembly 32 is configured to contain and/or absorb exudates discharged from the wearer. For example, the containment flaps 46 are configured to provide a barrier to the transverse flow of body exudates. A flap elastic member 53 (FIG. 5) can be operatively joined with each containment flap 46 in any suitable manner. The elasticized containment flaps 46 define a partially unattached edge which assumes an upright configuration in at least the crotch region 26 of the diaper pant 20 to form a seal against the wearer's body during use. In one suitable embodiment, the containment flaps 46 are located along the side edges 36 of the pant 20, and extend longitudinally along the entire length of the absorbent assembly 32. In other suitable embodiments, the containment flaps 46 only extend partially along the length of the absorbent assembly 32.

With reference now to FIGS. 1 and 2, the exemplary embodiment of the pant 20 illustrated therein includes a front waist elastic member 54 and a back waist elastic member 56 defining a waist band of the diaper pant 20. The waist elastic members 54, 56 can be formed of any suitable elastic material. Exemplary suitable elastic materials include, for example, sheets, strands or ribbons of natural rubber, synthetic rubber, or thermoplastic elastomeric polymers.

In the illustrated embodiment, both the front and back waist elastic members 54, 56 are generally rectangular in shape having a top edge 90, a bottom edge 92, and two side edges 94. As seen in FIG. 4, the top edges 90 of the front and back waist elastic members 54, 56 of the illustrated embodiment are generally aligned with the front waist edge 38 and back waist edge 39, respectively, of the pant 20 and, more specifically, the outer cover 40. It is understood, however, that the top edges 90 of the front waist elastic member 54 and/or the back waist elastic member 56 can be spaced from the front waist edge 38 of the pant 20 and/or the back waist edge 39 of the pant. That is, the top edges 90 of the front waist elastic member 54 and/or the back waist elastic member 56 can be spaced either above or below the front waist edge 38 of the pant 20 and/or the back waist edge 39 of the pant.

In one suitable embodiment, the front and back waist elastic members 54, 56 are point bonded to the pant 20 via a plurality of point bonds (not shown). In one such configuration, the point bonds are generally aligned in longitudinally extending rows with each of the rows being generally uniformly spaced apart, which provides uniform gathers in the front and back waist elastic members 54, 56. While the bond points can have various sizes and shape, in one suitable configuration, the bond points are generally circular and have a diameter of less than about 10 millimeters and suitably, between about 0.5 millimeters and about 3 millimeters. For example, the bond points can have a diameter of approximately 1 millimeter. It is understood, however, that the bond points can have any suitable size or shape.

In one suitable embodiment and as seen in FIGS. 1 and 4, the front and back waist elastic members 54, 56 are disposed on the outer cover 40. Thus, during use of the diaper pant 20, the front and back waist elastic members 54, 56 are readily visible. It is contemplated, however, that the front waist elastic member 54 and/or the back waist elastic member 56 can be disposed on the body-side liner 42 such that the elastic member faces the wearer during use. It is also contemplated that the front waist elastic member 54 and/or the back waist elastic member 56 can be disposed between the body-side liner 42 and the outer cover 40.

In one suitable embodiment, the presence or noticeability of the front waist elastic member 54 and/or the back waist elastic member 56 can be enhanced by providing suitable visual and/or tactile cues (e.g., graphics, texturing) on the waist elastic member(s). The visual and/or tactile cues can be provided to increase the noticeability that the front and back waist elastic members 54, 56 cooperate during use to fully encircle the waist of the wearer. In the illustrated embodiment, for example, both the front and back waist elastic members 54, 56 are a different color than the outer cover 40.

In the illustrated embodiment and as mentioned above, the front waist elastic member 54 and the back waist elastic member 56 cooperative during use of the pant to fully encircle the waist of the wearer. That is, the front and back waist elastic members 54, 56 cooperative fully encircle the waist opening 50 of the pant 20.

It is understood, however, that in other suitable embodiments of the pant 20, the front waist elastic member 54 and the back waist elastic member 56 can extend less than entirely around the waist opening 50. In one such configuration, the at least one of the front waist elastic member 54 and the back waist elastic member 56 does not extend beyond the respective ears 34, 134. In other words, the front waist elastic member 54 comprises a pair of segments with each of the segments being attached to one of the front ears 34, and/or the back waist elastic member 56 comprises a pair of segments with each of the segments being attached to one of the back ears 134. In one suitable configuration, neither the front waist elastic member 54 nor the back waist elastic member 56 corresponds to the location of the absorbent assembly 32. That is, both the front waist elastic member 54 and the back waist elastic member 56 terminate outboard of the side edges of the absorbent assembly 32.

The front and back waist elastic members 54, 56 can be formed of any suitable elastic material. Suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one suitable embodiment, for example, the front and back waist elastic members 54, 56 can comprise a plurality of dry-spun coalesced multifilament spandex elastomeric threads sold under the trade name LYCRA® and available from Invista of Wichita, Kans., U.S.A.

Other suitable materials from which the front and back waist elastic members 54, 56 may be constructed include vertical filament laminate (VFL) materials, elastic nonwoven composites having an apertured elastic film laminated to one or more nonwoven web materials, single- and dual-faced spandex laminates, stretch-bonded laminates (SBL), and continuous filament stretch-bonded laminates (CFSBL). A VFL is a composite material having at least one gatherable layer such as a non-woven material and at least one elastic layer. One type of vertical filament laminate is disclosed, for example, by U.S. Pat. No. 6,916,750 to Thomas et al., which is incorporated herein by reference. Examples of elastic nonwoven composites having an apertured elastic film laminated to one or more nonwoven web materials are described in U.S. Pat. No. 7,803,244 issued Sep. 28, 2010 to Siqueira et al., and U.S. Pat. No. 8,361,913 issued Jan. 29, 2013 to Siqueira et al., both of which are incorporated herein by reference. Examples of single- and dual-faced spandex laminates, SBLs, and CFS-BLs are described in U.S. Pat. No. 5,385,775 issued Jan. 31, 1995 to Wright; U.S. Pat. No. 6,057,024 issued May 2, 2000 to Mleziva et al.; and U.S. Pat. No. 6,969,441 issued Nov. 29, 2005 to Welch et al., all of which are incorporated herein by reference.

To further enhance containment of body exudates, the diaper pant 20 also includes a pair of leg cuff members 58. Each of the leg cuff members 58 extend at least partially about one of the leg openings 52, and preferably as seen in the illustrated embodiment, each of the leg cuff members 58 extend about the entirety of the respective leg opening. Thus, each of the leg cuff members 58 define one of the leg openings 52. During use of the pant 20, the leg cuff members 58 form a seal or gasket with the entire circumference of the legs (i.e., the upper thigh) of the wearer to thereby inhibit leakage of body exudates from between the pant and the wearer's legs.

In one suitable embodiment and as best seen in FIG. 4, each of the leg cuff members 58 extend along a respective one of the side edges 36 of the diaper pant 20 from the front waist edge 38 to the back waist edge 39. Thus in the illustrated embodiment, the leg cuff members 58 extend the entire longitudinally length of the diaper pant 20. More specifically, each of the illustrated leg cuff members 58 includes a first, front waist end 60 generally aligned with the top edge 90 of the front waist elastic members 54 and thus with the front waist edge 38 of the pant 20, and a second, back waist end 62 generally aligned with the top edge 90 of the back waist elastic members 56 and thus with the back waist edge 39 of the pant 20.

As illustrated in FIG. 4, the front waist end 60 of each of the leg cuff members 58 overlaps with and is bonded to or otherwise operatively connected to the front waist elastic member 54, and the back waist end 62 of each of the leg cuff members overlaps with and is bonded to or otherwise operatively connected to the back waist elastic member 56. As a result in the wear configuration of the diaper pant 20, the front waist ends 60 of the leg cuff members 58 are operatively connected to the front waist elastic member 54 such that the front waist ends move with the front elastic member during stretching and retraction of the front elastic member. Likewise, the back waist ends 62 of the leg cuff members 58 are operatively connected to the back waist elastic member 56 such that the back waist ends move with the back elastic member during stretching and retraction of the front elastic member.

It is understood, however, that in some suitable embodiments of the diaper pant 20, the leg cuff members 58 can extend less than the entire longitudinal length of the diaper pant. In such an embodiment, the front waist end 60 of each of the leg cuff members 58 will be spaced from the front waist edge 38 of the pant 20, and the back waist end 62 will be spaced from the back waist edge 39 of the pant 20. However, the front waist ends 60 of the leg cuff members 58 should be disposed on or in sufficiently close proximity to the front waist elastic member 54 so that the front waist ends move with the front elastic member during stretching and retraction of the front elastic member. Likewise, the back waist ends 62 of the leg cuff members 58 should be disposed on or in sufficiently close proximity to the back waist elastic member 56 so that the back waist ends move with the back elastic member during stretching and retraction of the front elastic member.

In the illustrated embodiment, the leg cuff members 58 are attached to the garment-facing surface 30 of the outer cover 40 as seen in FIG. 4. In one suitable embodiment, for example, the leg cuff members 58 can be point bonded to the pant 20 via a plurality of bond points (not shown). While the bond points can have various sizes and shape, in one suitable configuration, the bond points are generally circular and have a diameter of less than about 5 millimeters and suitably, between about 0.5 millimeters and about 3 millimeters. For example, the bond points can have a diameter of approximately 1 millimeter. It is understood, however, that the bond points can have any suitable size or shape. It is understood, however, that the leg cuff members 58 can be attached to the body-facing surface 28 of the bodyside liner 42, or between the outer cover 40 and bodyside liner 42.

As mentioned above, the leg cuff members 58 of the illustrated embodiment are disposed on the garment-facing surface 30 of the outer cover 40. Thus, during use of the diaper pant 20, the leg cuff members 58 are readily visible. In one suitable embodiment, the presence or noticeability of the leg cuff members 58 can be enhanced by providing suitable visual and/or tactile cues (e.g., graphics, texturing) on the leg cuff members. The visual and/or tactile cues can be provided to increase the noticeability that the leg cuff members 58. In the illustrated embodiment, for example, leg cuff members 58 are a different color than the outer cover 40.

The leg cuff members 58 can be formed from any suitable elastic or non-elastic material. In one suitable embodiment, for example, each of the leg cuff members 58 can be formed from a non-elastic spunbond web. "Spunbond web" generally refers to a web containing small diameter, substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 microns, and are often between about 5 to about 20 microns. To provide additional web integrity, the webs so formed can be subjected to additional fiber bonding techniques if so desired. See for example, U.S. Pat. No. 3,855,046 to Hansen et al., which is incorporated herein in its entirety by reference thereto for all purposes. Other suitable non-elastic material of forming the leg cuff members 58 can be SMS, melt blown polyolefin or other non-elastic polyolefin.

Suitable elastic materials for the leg cuff members 58 include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one suitable embodiment, for example, the leg cuff members 58 can comprise a plurality of dry-spun coalesced multifilament spandex elastomeric threads sold under the trade name LYCRA® and available from Invista of Wichita, Kans., U.S.A.

Other suitable materials from which the leg cuff members 58 may be constructed include vertical filament laminate (VFL) materials, elastic nonwoven composites having an apertured elastic film laminated to one or more nonwoven web materials, single- and dual-faced spandex laminates, stretch-bonded laminates (SBL), and continuous filament stretch-bonded laminates (CFSBL). A VFL is a composite material having at least one gatherable layer such as a nonwoven material and at least one elastic layer. One type of vertical filament laminate is disclosed, for example, by U.S. Pat. No. 6,916,750 to Thomas et al., which is incorporated herein by reference. Examples of elastic nonwoven composites having an apertured elastic film laminated to one or more nonwoven web materials are described in U.S. Pat. No. 7,803,244 issued Sep. 28, 2010 to Siqueira et al., and U.S. Pat. No. 8,361,913 issued Jan. 29, 2013 to Siqueira et al., both of which are incorporated herein by reference. Examples of single- and dual-faced spandex laminates, SBLs, and CFSBLs are described in U.S. Pat. No. 5,385,775 issued Jan. 31, 1995 to Wright; U.S. Pat. No. 6,057,024 issued May 2, 2000 to Mleziva et al.; and U.S. Pat. No. 6,969,441 issued Nov. 29, 2005 to Welch et al., all of which are incorporated herein by reference.

As noted previously, the illustrated diaper pant 20 includes front and back ears 34, 134 that cooperatively define transversely opposite sides of the pant 20 in the wear configuration. As illustrated in FIGS. 1-3, the back ears 134 overlap and are attached to the respective front ears 34. Thus, the back ears 134 overlap and cover the front waist ends 60 of the leg cuff members 58. It is contemplated that the front ears 34 can overlap the respective back ears 134 such that the back waist ends 62 of the leg cuff members 58 are covered by (i.e., underlie) the front ears. The front and back ears 34, 134 can be permanently attached to each other along one or more attachment seams (not shown). The ears 34, 134 may be attached to each other using any suitable attachment means such as, for example, adhesives, ultrasonic bonds, thermal bonds, pressure bonds, or combinations thereof. It is also understood that the leg cuff members 58 can be fully disposed on the garment-facing surface 30 of the pant 20 such that the entire leg cuff member is readily visible.

With reference to FIGS. 4 and 5, each of the illustrated front and back ears 34, 134 are generally triangular in shape have a leg end edge 70 disposed toward the longitudinal center of the diaper pant 20, and a waist end edge 72 disposed toward a longitudinal end of the diaper pant 20. The leg end edge 70 and waist end edge 72 extend from the side edges of the absorbent assembly 32 (FIG. 5). The leg end edges 70 of the front and back ears 34, 134 form part of the side edges 36 of the diaper pant 20. One or more of the leg end edges 70 (i.e., the leg end edges of the front ears 34 and/or the leg end edges of the back ears 134) may be suitably curved and/or angled relative to the transverse axis 49 to provide a better fit around the wearer's legs. The waist end edges 72 of the front ears 34 form part of the front waist edge 38 of the diaper pant 20, and the waist end edges 72 of the back ears 134 form part of the back waist edge 39 of the pant 20. It is understood that the ears 34, 134 can have any suitable shape including, for example, square, rectangular.

In one suitable embodiment, the front and back ears 34, 134 suitably comprise a stretchable material capable of stretching in at least a direction generally parallel to the transverse axis 49 of the diaper pant 20 (FIGS. 4 and 5). More suitably the ears 34, 134 comprise an elastic material. Suitable elastic materials, as well as one process of incorporating stretchable ears into pants, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the stretch material may comprise a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference. In other suitable embodiments, the front and back ear material may comprise other woven or nonwoven materials, such as the materials described above as being suitable for the outer cover 40 or bodyside liner 42, mechanically pre-strained composites, stretchable but inelastic materials, and combinations thereof.

As seen in FIG. 3, which illustrates one of the leg cuff members 58 (i.e., the left leg cuff member of the diaper pant 20), each of the leg cuff members are generally "ϓ" shaped. More specifically, each of the illustrated leg cuff members 58 has a lower, generally teardrop-shaped portion 66 and an upper, generally "V" shaped portion 68 extending between the teardrop-shaped portion 66 and the front waist elastic member 54 and the back waist elastic member 56. More specifically, one of the legs or segments 68' of the "V" shaped portion 68 extends between the teardrop-shaped portion 66 and the front waist elastic member 54, and the other leg or segment 68" of the "V" shaped portion extends between the teardrop-shaped portion and the back waist elastic member 56. The teardrop-shaped portion 66 defines the leg openings 52. An apex 80 of openings 52 defined by the teardrop-shaped portion 66 also corresponds to the base or lowest most point of the "V" shaped portion.

As seen in FIG. 3, which illustrates the pant 20 in a relaxed state of the wear configuration, the segments 68', 68" of the "V" shaped portion 68 are spaced apart by a first distance D1. The distance D1 is the spacing between the inside edges of the segments 68', 68" at their greatest longitudinal extent, which in the illustrated embodiment corresponds with the front waist edge 38 and the back waist edge 39 of the pant 20. In one suitable embodiment, the distance D1 is between about 2 inch and about 8 inches, and more specifically between about 3 inches and about 6 inches. In one particularly suitable embodiment, for example, the distance D1 is approximately 5 inches.

In one suitable embodiment, for example, the waist opening 50 of the diaper pant 20, which is defined by the front waist elastic member 54 and the back waist elastic member 56, has in the relaxed state of the wear configuration a circumference of the about 14 inches. Thus, in an embodiment having a waist opening with a 14 inch circumference and a 5 inch distance D1 between the segments 68', 68" of the "V" shaped portion 68, the ratio between the distance D1 and the circumference is about 1:3 (i.e., 1:2.8). Other suitable ratios between the distance D1 and the circumference of the waist opening 50 include, for example, between about 1:7 and about 1:1.75 and more specifically between about 1:5 and about 1:2. It is contemplated that the distance D1 and the circumference of the waist opening 50 can define any suitable ratio without departing from some aspects of the present disclosure.

With reference still to FIG. 3, the circumference of the leg openings 52, which are defined by the teardrop portions 66 of the leg cuff members 58, are proportional to the circumference of the waist opening 50 of the pant 20. In the illustrated embodiment, for example, the ratio between the circumference of the leg openings 52 (which is approximately 5 inches) and the circumference of the waist opening 50 in the relaxed state of the wear configuration is approximately 1:2.8. It is contemplated, however, that the diaper pant 20 can have any suitable ratio between the circumference of the leg openings 52 and the circumference of the waist opening 50 in the relaxed state of the wear configuration.

In one suitable embodiment, the ratio between the distance D1 and the circumference of the waist opening 50 and the ratio between the circumference of the leg openings 52 and the circumference of the waist opening, in the relaxed state of the wear configuration, are approximately equal. For example, in the illustrated embodiment, both ratios are approximately 1:2.8. Stated another way, in the illustrated embodiment, the distance D1 between the segments 68', 68" of the "V" shaped portion 68 is approximately equal to the circumference of the leg openings 52. It is contemplated, however, that the distance D1 between the segments 68', 68" of the "V" shaped portion 68 can be different than the circumference of the leg openings 52 without departing from some aspects of this disclosure.

Figure 6:
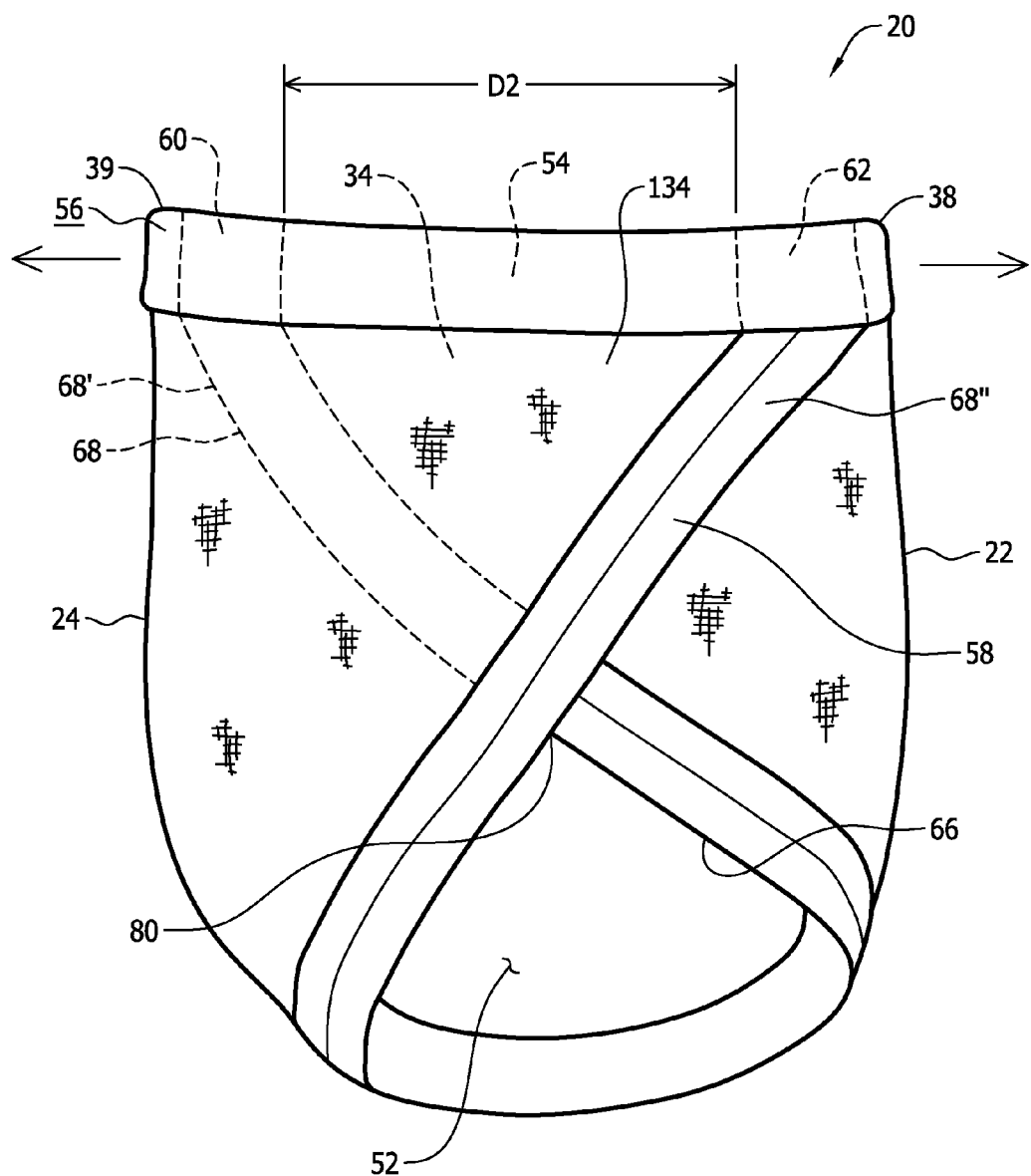
FIG. 6 is an enlarged side view of the diaper showing the waist band and interconnect leg cuff member in a relaxed condition.

With reference now to FIGS. 3 and 6, during use of the diaper pant 20, the front waist elastic member 54 and the back waist elastic member 56 will stretch and contract during movement and activities conducted by the wearer and/or care giver. For example, the front waist elastic member 54 and the back waist elastic member 56 will be stretched, in the direction indicated by arrows in FIG. 6, upon donning the diaper pant 20 on the child. As the front waist elastic member 54 and the back waist elastic member 56 stretches, the ends of the leg cuff members 58, which are bonded to or near the waist elastic members, will be moved apart.

Moving the segments 68', 68" of the "V" shaped portion 68 of the leg cuff members 58 apart results in the circumference of the leg openings 52, which are defined by the lower teardrop-shaped 66 portion of the leg cuff members, to become smaller. That is, the size of the leg openings 52 is moved from a first, greater size in the relaxed wear configuration to a second, smaller size in the stressed, wear configuration. For example, when the distance D1 between the segments 68', 68" of the "V" shaped portion 68 in the relaxed state of the wear configuration (FIG. 3) is increased to a second, greater distance D2 in a stretched (or stressed) state of the wear configuration (FIG. 6), the size of the circumference of the leg openings 52 is decreased.

Thus, as the front waist elastic member 54 and the back waist elastic member 56 stretches about the wearer's waist during use of the diaper pant 20, each of the leg cuff members 58 tighten and thereby form a greater seal against the legs of the wearer. Conversely, as the front waist elastic member 54 and the back waist elastic member 56 contract or otherwise relax about the wearer's waist during use of the diaper pant 20, each of the leg cuff members 58 loosen about the legs of the wearer. Thus, the leg cuff members 58 of the present disclosure provide a dynamic fit about the wearer's legs during use of the diaper pant 20. As a result, the leg cuff members 58 provide a sufficient seal against the wearer's body during use and particularly prolonged use of the pant 20 while inhibiting irritation or marking of the wearer's legs.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An absorbent article having a body-facing side and a garment-facing side, the absorbent article comprising:
a bodyside liner, an outer cover, and an absorbent structure disposed between the outer cover and the bodyside liner;
a front waist region, a back waist region, and a crotch region extending between the front waist region and the back waist region, the front waist region having a front waist edge and the back waist region having a back waist edge, the front and back waist edges defining a waist opening of the absorbent article when the absorbent article is in a wear configuration, an elastomeric waist band extending around at least a portion of the waist opening adjacent the front and back waist edges, the waist band defining a circumference of the waist opening; and
a pair of leg cuff members, each of the leg cuff members overlapping itself and defining a leg opening when the absorbent article is in the wear configuration and operatively connected to the waist band such that movement of the waist band results in movement of the leg cuff members, each of the leg cuff members having a lower, generally teardrop-shaped portion and an upper, generally "V" shaped portion extending between the teardrop-shaped portion and the waist band, the "V" shaped portion defining a first segment and a second segment spaced from the first segment by a distance D1, a ratio between the distance D1 and the circumference of the waist band being between 1:1.75 and 1:7 in a relaxed state of the wear configuration, each of the leg cuff members extending along a respective side edge of the absorbent article from the front waist edge to the back waist edge when the absorbent article is in an unfolded and laid flat configuration.

2. The absorbent article set forth in claim 1 wherein the ratio between the distance D1 and the circumference of the waist band is between 1:2 and 1:5.

3. The absorbent article set forth in claim 2 wherein the ratio between the distance D1 and the circumference of the waist band is about 1:3.

4. The absorbent article set forth in claim 1 wherein the distance D1 is between 2 inch and 8 inches.

5. The absorbent article set forth in claim 4 wherein the distance D1 is between 3 inches and 6 inches.

6. The absorbent article set forth in claim 5 wherein the distance D1 is approximately 5 inches.

7. The absorbent article set forth in claim 1 wherein each of the leg cuff members defines a circumference of the respective leg opening, a ratio between the circumference of the leg openings and the circumference of the waist opening being approximately equal to the ratio between the distance D1 and the circumference of the waist opening in the relaxed state of the wear configuration.

8. The absorbent article set forth in claim 1 wherein each of the leg cuff members is formed from a non-elastic material.

9. The absorbent article set forth in claim 8 wherein the non-elastic material comprises a spunbond web.

10. The absorbent article set forth in claim 1 wherein the elastomeric waist band comprises a front waist elastic member disposed in the front waist region adjacent the front waist edge and a back waist elastic member bonded to the front waist elastic member disposed in the back waist region adjacent the back waist edge, each of the leg cuff members being bonded to the front waist elastic member and the back waist elastic member.

11. The absorbent article set forth in claim 10 wherein each of the leg cuff members is formed from a non-elastic material.

12. The absorbent article set forth in claim 11 wherein the non-elastic material comprises a spunbond web.

13. The absorbent article set forth in claim 1 further comprising a pair of front ears disposed in the front waist region and a pair of back ears disposed in the back waist region, each of the back ears overlapping a respective one of the front ears in the wear configuration.

14. The absorbent article set forth in claim 13 wherein each of the front and back ears are generally triangular in shape have a leg end edge and a waist end edge.

15. The absorbent article set forth in claim 1 wherein each of the leg cuff members includes a front waist end generally aligned with the front waist edge of the absorbent article, and a back waist end generally aligned with the back waist edge of the absorbent article.

16. The absorbent article set forth in claim 15 wherein each of the leg cuff members is formed from a non-elastic material.

17. The absorbent article set forth in claim 1 wherein the cuff members are attached to the outer cover on the garment-facing side of the absorbent article.

18. The absorbent article set forth in claim 17 wherein the leg cuff members comprise at least one of a visual cue and a tactile cue.

* * * * *